United States Patent [19]

Danko

[11] Patent Number: 5,659,390
[45] Date of Patent: Aug. 19, 1997

[54] METHOD AND APPARATUS FOR DETECTING PARTICLES ON A SURFACE OF A SEMICONDUCTOR WAFER HAVING REPETITIVE PATTERNS

[75] Inventor: Joseph J. Danko, Franklin, Mass.

[73] Assignee: Inspex, Inc., Billerica, Mass.

[21] Appl. No.: 386,289

[22] Filed: Feb. 9, 1995

[51] Int. Cl.[6] ................................................ G01N 21/00
[52] U.S. Cl. ................................. 356/237; 250/559.41
[58] Field of Search ........... 356/237; 250/559.4–559.41, 250/0.45–0.46

[56] References Cited

U.S. PATENT DOCUMENTS

| | | | |
|---|---|---|---|
| 4,806,774 | 2/1989 | Lin et al. | 356/237 |
| 5,046,847 | 9/1991 | Nakata et al. | 356/237 |
| 5,090,807 | 2/1992 | Tai | 356/330 |
| 5,276,498 | 1/1994 | Galbraith et al. | 356/237 |

Primary Examiner—Frank G. Font
Assistant Examiner—Jason D. Vierra Eisenberg
Attorney, Agent, or Firm—Kriegsman & Kriegsman

[57] ABSTRACT

An apparatus for detecting particles on the front surface of a patterned semiconductor wafer having repetitive patterns includes a laser for illuminating an area on the front surface at grazing angle of incidence with a beam of polarized light. A lens collects light scattered from the area and forms a Fourier diffraction pattern of the area illuminated. A Fourier mask blocks out light collected by the lens at locations in the Fourier diffraction pattern where the intensity is above a predetermined level indicative of background information and leaves in light at locations where the intensity is below the threshold level indicative of possible particle information. The Fourier mask includes an optically addressable spatial light modulator and a crossed polarizer with the Fourier diffraction pattern being used as both a read beam and a write beam for the spatial light modulator. A camera detects scattered light collected from the area by the lens and not blocked out by the Fourier mask.

5 Claims, 3 Drawing Sheets

METHOD AND APPARATUS FOR DETECTING PARTICLES ON A SURFACE OF A SEMICONDUCTOR WAFER HAVING REPETITIVE PATTERNS

BACKGROUND OF THE INVENTION

The present invention relates generally to a method and apparatus for detecting the presence of particles on the surface of an object and more particularly to a method and apparatus for detecting contaminant particles on the surface of a patterned semiconductor wafer having repetitive patterns using the principle of light scatttering. An example of a patterned semiconductor wafer having repetitive patterns is a memory wafer.

There are a variety of existing ways for detecting and measuring the number and sizes of particles on the surface of a semiconductor wafer for the purpose of rejecting those wafers which have on their surface one or more particles above certain sizes or an excessive number of particles. One of the more simple methods involves having a human operator inspect the wafer using a light field/dark field microscope. Using the eye, the operator actually counts the number of particles and also identifies the size of the particles, such as those between 1 and 20 microns, and then rejects those wafers which have particles of or above a certain size or which have an excessive number of particles. This method, however, is highly inaccurate and very expensive both in terms of wages for the human operator and in terms of the number of rejects both after the inspection and after production of the chips (when an erroneously passed wafer is found to have an electrical defect, e.g., show circuits, because of the presence of contaminant particles).

In U.S. Pat. No. 5,317,380, issued May 31, 1994, and assigned to Inspex, Inc. there is disclosed a method and apparatus for detecting particles on a surface of an object, such as a virgin or patterned semiconductor wafer, ceramic tile, or the like. In one embodiment, an apparatus is provided in which a scanning beam of laser light is brought to focus as an arcuate scan line on a surface of the object at a grazing angle of incidence using an off-axis hypertelecentric mirror. A pair of light detectors are positioned at a meridional angle of about 30 degrees and at an azimuthal angle of about 4 degrees to measure forward scattered light from the surface. The object is then moved translationally so that the beam can scan another line of the surface. A light trap is provided to trap light that is reflected by the surface, and a series of masks are provided to mask light which is scattered by the hypertelecentric mirror and in the case of pattered objects, light which is diffracted by the pattern imprinted on the object.

In U.S. Pat. No. 4,898,471, issued Feb. 6, 1990, and assigned to Tencor Instruments, a system for detecting particles and other defects on a patterned semiconductor wafer, photomask, or the like is disclosed. The system includes a light source for emitting a beam of light. A polarizing filter is used to polarize the beam of light in a direction substantially parallel to the surface of the patterned semiconductor wafer to be examined. The beam is enlarged in cross-sectional diameter by a beam expander placed along the path of the beam after the polarizing filter. The beam is then caused to scan by a deflection mirror. A telecentric lens brings the scanning beam to focus on the patterned wafer at a shallow angle of incidence, the beam striking the wafer surface substantially parallel to the pattern streets formed on the wafer. A light collection system for detecting side scattered light is positioned in the plane of the scan line. The light collection system, which includes a lens for focusing the side scattered light, a polarizing filter oriented in a direction substantially parallel to the surface of the patterned wafer, and a photomultiplier tube for detecting light incident thereon and transmitting electrical signals in response thereto, receives light scattered in a direction less than 15 degrees above the surface and at angel relative to the beam direction in a range from about 80 degrees to 100 degrees. A processor constructs templates from the electrical signal corresponding to individual patterns and compares the templates to identify particles.

In U.S. Pat. No. 4,806,744 issued Feb. 21, 1989 and assigned to Insystems, Inc., there is disclosed an inspection system which employs a Fourier transform lens and an inverse Fourier transform lens positioned along an optic axis to produce from an illuminated area of a patterned specimen wafer a spatial frequency spectrum whose frequency components can be selectively filtered to produce an image pattern of defects in the illuminated area of the wafer. Depending on the optical components configuration of the inspection system, the filtering can be accomplished by a spatial filter of either the transmissive or reflective type. The lenses collect light diffracted by a wafer die aligned with the optic axis and light diffracted by other wafer dies proximately located to such die. The inspection system is useful for inspecting only dies having many redundant circuit patterns. The filtered image strikes the surface of a two-dimensional photodetector array which detects the presence of light corresponding to defects in only the illuminated on-axis wafer die. Inspection of all possible defects in the portions of the wafer surface having many redundant circuit patterns is accomplished by mounting the wafer onto a two-dimensional translation stage and moving the stage so that the illuminated area continuously scans across the wafer surface from die to die until the desired portions of the wafer surface have been illuminated. The use of a time delay integration technique permits continuous stage movement and inspection of the wafer surface in a raster scan fashion.

In U.S. Pat. No. 4,895,446 to M. C. Maldari et al., there is disclosed a method and apparatus for detecting the presence of particles on the surface of an object such as the front side of a patterned semiconductor wafer. A vertically expanded, horizontally scanning, beam of light is directed onto an area on the surface of the object at grazing angle of incidence. A video camera positioned above the surface detects light scattered from any particles which may be present on the surface, but not specularly reflected light. The surface is angularly repositioned (rotated) relative to the incident light beam so that the diffracted light form the surface and the pattern of lines on the surface is at a minimum. The object is then moved translationally to expose another area to the incident light beam so that the entire surface of the object or selected portions thereof can be examined, one area at a time. The patent also discloses the use of a mark containing a pattern corresponding to the Fourier transform of the patterned surface to mask off light scattered from the pattern on the surface but not any particles that may be present on the surface.

In U.S. Pat. No. 4,377,340 to G. P. Green et al., there is disclosed a method and apparatus for detecting and measuring the number and sizes of impurities on the surface of a material, such as a semiconductor wafer, wherein a beam of high intensity collimated light from a xenon arc lamp is directed onto the surface at normal incidence in the absence of any extraneous light, through a collimating mirror and a pin hole device and where at the particles will scatter the light, and wherein the surface is viewed by a high light sensitive TV camera which is positioned off-axis to pick up scattered light but not specularly reflected light for display on a viewing screen.

In U.S. Pat. No. 4,342,515 to M. Akiba et al., there is disclosed an inspection apparatus for detecting unfavorable foreign matters existent on the surface of an object such as a semiconductor wafer. The apparatus includes a collimated beam generator portion which projects a collimated beam towards the object to be inspected from a side thereof and a mechanism which senses light reflected from the surface of the object, through a polarizer plate. In accordance with the disclosed technique for using the apparatus, the signal-to-noise ratio between a detection signal generated by a pattern of the foreign matter to be detected and a signal generated by a normal pattern of the object surface and sensed as a noise component are said to be enhanced.

In U.S. Pat. No. 3,782,836 to D. F. Fey et al., there is disclosed a surface irregularity analyzing system which includes structure for directing light toward a surface in a direction having a certain angular relationship to the surface. If the light strikes irregularities in the surface it is reflected in a direction having an angular relationship to the surface other than equal and opposite the incident direction. The amount of light reflected from irregularities in the surface is determined, either photographically or photoelectrically using a detector positioned over the surface, to provide an analysis of irregularities in the surface.

In U.S. Pat. No. 2,947,212 to R. C. Woods, there is disclosed a method of detecting surface conditions on a strip of sheet metal having line markings in which light from a light source is directed towards the surface of the sheet metal in a direction generally perpendicular to the line markings. Non-specular reflection in a selected direction which is perpendicular to the lines, and which is preferably between the angle of incidence and the angle of specular reflection, is monitored by a photoelectric cell which is able to detect a surface flaw by variation in the intensity of the reflected light. The light in the incident beam may be polarized and the light in the selected non-specular reflected beam filtered to pass only such polarized light.

SUMMARY OF THE INVENTION

It is an object of the present invention to provide a new and improved method and apparatus for detecting the presence of contaminant particles on the surface of a patterned semiconductor wafer having repetitive patterns using the principle of scattered light.

It is another object of the present invention to provide a method and apparatus as described above in which background scatter is filtered out in a new and novel manner.

It is a further object of the present invention to provide a method and apparatus as described above which is designed for use in dark field and bright field illumination applications.

Other objects, as well as features and advantages of the present invention, will be set forth in part in the description which follows, and in part will be obvious from the description or may be learned by practice of the invention. The objects, features, and advantages of the invention may be realized and attained by means of the instrumentalities and combinations particularly pointed out in the appended claims.

Apparatus for detecting particles on the front surface of a patterned semiconductor wafer having repetitive patterns according to this invention comprises means for illuminating an area on said front surface with a beam of polarized light, optical means for collecting light scattered from the area illuminated, the optical means forming a Fourier diffraction pattern of area illuminated, self-programmable Fourier mask means for blocking out from the light collected by the optical means areas in the Fourier diffraction pattern whose intensity is above a predetermined level indicative of background information and letting pass through areas in the Fourier diffraction pattern whose intensity is below the threshold level indicative of possible particle information, the Fourier mask means including an optically addressable spatial light modulator and a crossed polarizer, and a camera for detecting light scattered from area collected by the optical means and not blocked out by the Fourier mask means.

A method for detecting particles on the front surface of a patterned semiconductor wafer having repetitive pattern according to this invention comprises illuminating an area on the front surface with a beam of polarized light, collecting light scattered from the area illuminated and forming a Fourier diffraction pattern of the light scattered from the area illuminated, blocking out from the light collected areas in the Fourier diffraction pattern whose intensity is above a predetermined level indicative of background information and letting pass through areas in the Fourier diffraction pattern whose intensity is below the threshold level indicative of possible particle information, the blocking being achieved using an optically addressable spatial light modulator which rotates the polarization of the Fourier diffraction pattern at locations where the intensity is below a predetermined threshold level and a crossed polarizer, and detecting scattered light collected from the area illuminated and not blocked out.

BRIEF DESCRIPTION OF THE DRAWINGS

In the drawings wherein like reference numerals represent like parts.

DETAILED DESCRIPTION OF PREFERRED EMBODIMENTS

The present invention is directed to a method and apparatus for detecting the presence of contaminant particles on the surface of a patterned semiconductor wafer having repetitive patterns using the principle of scattered light.

In accordance with the invention an area on the surface to be examined is illuminated with a beam of polarized light. A lens collects light scattered from the area illuminated and forms a Fourier diffraction pattern of the scattered light. A Fourier mask blocks out light in areas in the Fourier diffraction pattern above a predetermined intensity level indicative of background information on the wafer and does not block out light in areas which is below the predetermined intensity level indicative of possible particles. The unblocked light is then detected by a camera. The procedure is repeated for other areas on the surface.

The Fourier mask comprises an optically addressable spatial light modulator and a crossed polarizer.

Figure 1:
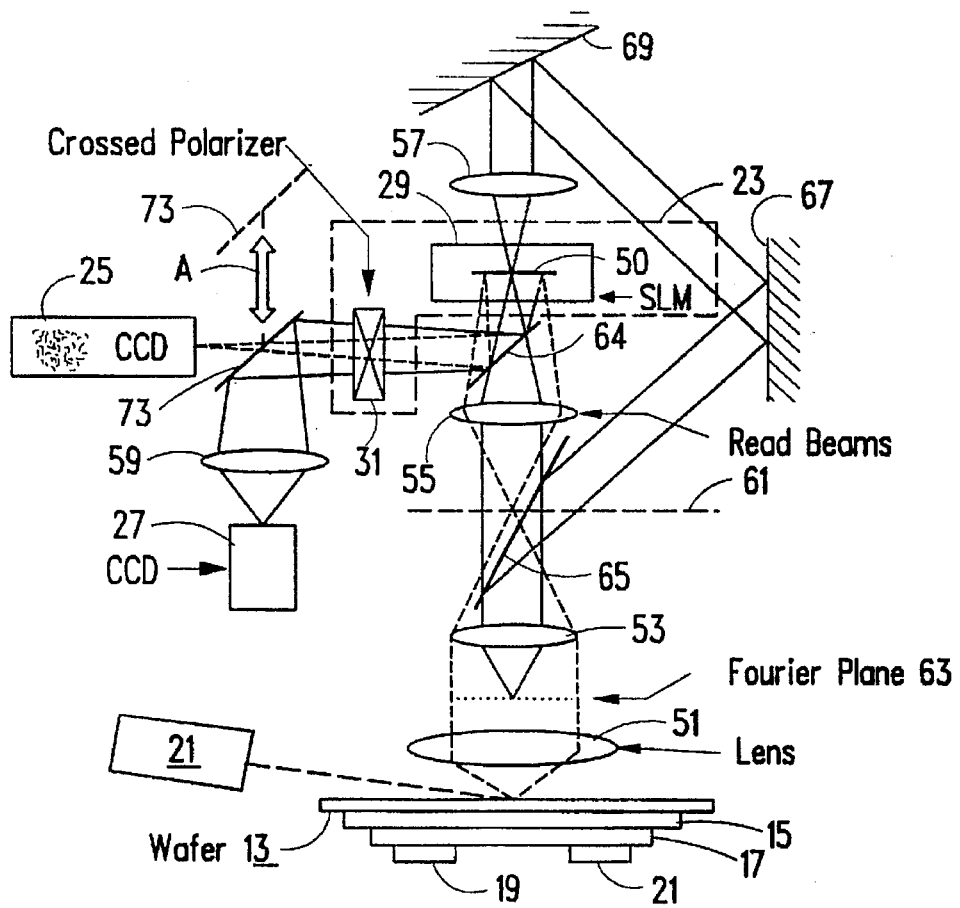
FIG. 1 is a schematic representation of an embodiment of an apparatus constructed according to the teaching of the present invention for detecting the presence of contaminant particles on the front surface of a patterned semiconductor wafer.

Referring now to the drawings there is illustrated in FIG. 1 an apparatus 11 for use in detecting the presence of particles on the front surface 12 surface of a patterned semiconductor wafer 13 having repetitive patterns.

Apparatus 11 includes a holder 15 for holding wafer 13. Holder 13 is mounted on a stage 17 which is movable in two mutually perpendicular directions by a pair of motors 19 and 21, the particular details of the mechanical arrangement for moving stage 17 not being a part of this invention.

Apparatus 11 also includes a light source 21, a self-programmable Fourier mask 23, a first light detector 25 and a second light detector 27.

Light source 21 generates a high intensity, plane polarized, coherent, monochromatic beam of light and may be, for example, a ND:YAG laser or a helium-neon laser.

Figure 2:
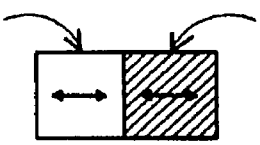
FIG. 2 is a detailed view of the spatial light modulator shown in FIG. 1 and one of the beamsplitters.
Figure 2:
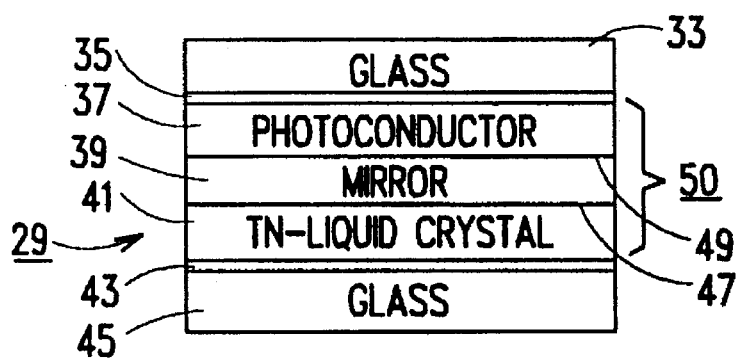
Figure 2:
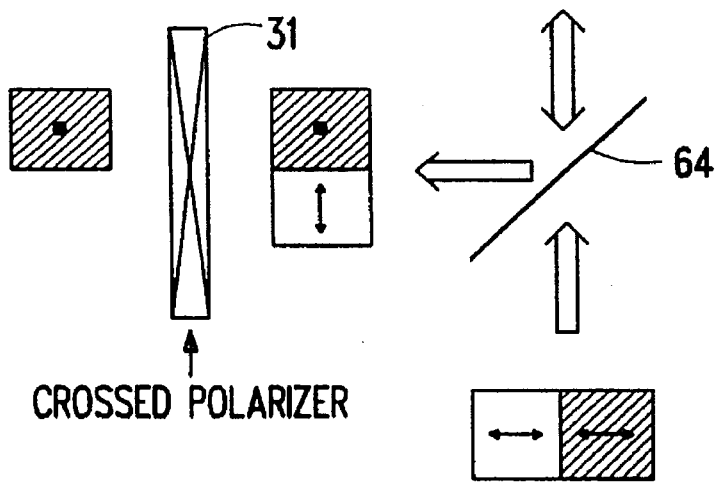

Self-programmable Fourier mask 23 which is shown in detail in FIG. 2 includes a liquid crystal spatial light modulator 29 and a crossed polarizer 31. Liquid crystal spatial light modulator 29 which is shown in detail in FIG. 2 includes a back layer of glass 33, a first transparent electrode 35 in front of back layer 33, a photoconductor 37, such as amorphous silicon, in front of first transparent electrode 35, a dielectric mirror 39 in front of photoconductor 37, a liquid crystal 41 in front of dielectric mirror 39, a second transparent electrode 43 in front of liquid crystal 41 and a front layer of glass 45 in front of second transparent electrode 43. Dielectric mirror 39 includes a front side 47 and a rear side 49. Liquid crystal spatial light modulator 29 is preferably a ferromagnetic liquid crystal type spatial light modulator. The thicknesses of layers 33, 37, 39, 41 and 45 may be as follows: layers 33 about 5 mm, layer 37 about 3 microns, layer 39 about 1 micron, layer 41 about 1 micron and layer 45 about 5 mm. For simplicity, layers 37, 39 and 41 on spatial light modulator 29 are shown in FIG. 1 as a single line 50. Electrodes 35 and 43 are on the order of about 1 micron thick.

First light detector 25 is a high sensitivity video camera and second light detector 27 may be a standard video camera. Each camera may be, for example, CCD type cameras.

Apparatus 11 also includes a first lens 51, a second lens 53, a third lens 55, a fourth lens 57 and a fifth lens 59.

In the operation of apparatus 11, light from source 21 is directed onto front surface 12 of semiconductor wafer 13. Light source 21 is arranged so as to strike surface 12 at a grazing angle of incidence i.e. at an angle of between around 0 and 5 degrees. Light scattered upward from the area on surface 12 which is illuminated by the beam of light from source 21 is imaged by first lens 51 in combination with second lens 53 at intermediate image plane 61. As can be appreciated, the image formed at intermediate image plane 61 includes light scattered from any particles which may be present on the area of the surface illuminated and, in addition, light scattered from the pattern lines of the pattern on the area of the surface illuminated. A Fourier diffraction pattern of the scattered light is formed at the back focal plane 63 of lens 51.

The image of area of surface 12 illuminated by light source 21 which is formed at intermediate image plane 61 passes through a beamsplitter 64 and is reimaged by third lens 55 at first light detector 25 after being reflected off mirror 39 and being reflected off beamsplitter 64. In Fourier mask 23 light whose intensity is above a predetermined intensity level and corresponding to pattern lines on the surface of wafer 13 is blocked out.

Second lens 53 in combination with third lens 55 forms an image of the Fourier diffraction pattern from plane 63 on liquid crystal 41 in spatial light modulator 29 after passing through beamsplitter 64 and from there is reflected off mirror 39. A portion of the light passed by lens 53 corresponding to the Fourier diffraction pattern is reflected off of a beamsplitter 65 located between lens 53 and lens 55, then reflected off of a pair of mirrors 67 and 69 and then in combination with fourth lens 57 enters spatial light modulator 29 from the rear and is brought to focus at photoconductor 37. Thus, lens 53 and lens 55 are used to image the Fourier diffraction formed at plane 63 on liquid crystal 41 while lens 53 and 57 along with beamsplitter 65 and mirrors 67 and 69 are used to image the Fourier diffraction pattern formed at plane 63 onto photoconductor 37. The beam of light striking mirror 47 from liquid crystal 41 constitutes a "read" beam while the beam of light striking photoconductor 37 constitutes a "write" beam. The write beam and read beam are axially aligned on their corresponding sides of mirror 39 and are of the same size (magnitude). Thus there is point to point correspondence of the write and read beams at spatial light modulator 39.

In those areas (locations) where the intensity of the write beam is below a predetermined threshold level indicative of possible particle information, the polarization of the corresponding areas on the read beam on reflection from mirror 39 will be rotated 90 degrees. On the other hand, in those areas where the write beam is above the preselected threshold level indicative of background information, the polarization of corresponding areas on the read beam on reflection from mirror 39 will remain the same; i.e. will not be rotated.

Light reflected from mirror 39 is deflected off beamsplitter 64 and strikes crossed polarizer 31 which allows areas on the beam where the polarization has been rotated 90 degrees to pass through and blocks areas on the beam where the polarization has not been rotated. Light passed through polarizer 31 is then brought to focus on detector 25.

Thus, detector 25 records an image of light scattered from surface 12 whose intensity is below the predetermined threshold level and caused by particles and not scattered light whose intensity is above the threshold level and caused by pattern lines.

Apparatus 11 also includes a beamsplitting mirror 73 which is movable up and down as shown by arrows A. When mirror 73 is in the position shown, the Fourier diffraction pattern after it is processed by Fourier mask 23 will be imaged by lens 59 onto detector 27 while the scattered light from surface 12 will be imaged onto detector 25 after it is processed by spatial light modulator 23. On the other hand, when mirror 73 is moved out the light path, as shown by the dotted lines only an image of the portion of wafer 11 illuminated, without the pattern lines, will be formed on camera 25 and no image will be formed on detector 27.

Wafer 13 is then moved translationally so that other areas on surface 12 may be examined, in a similar manner, one at a time.

As can be appreciated, mask 23 is self-programmable in that it is not limited to use with a wafer having a particular pattern of lines but rather can be used with any wafer having patterns that are repetitive, even if the diffraction pattern changes from area to area on the wafer.

Figure 3:
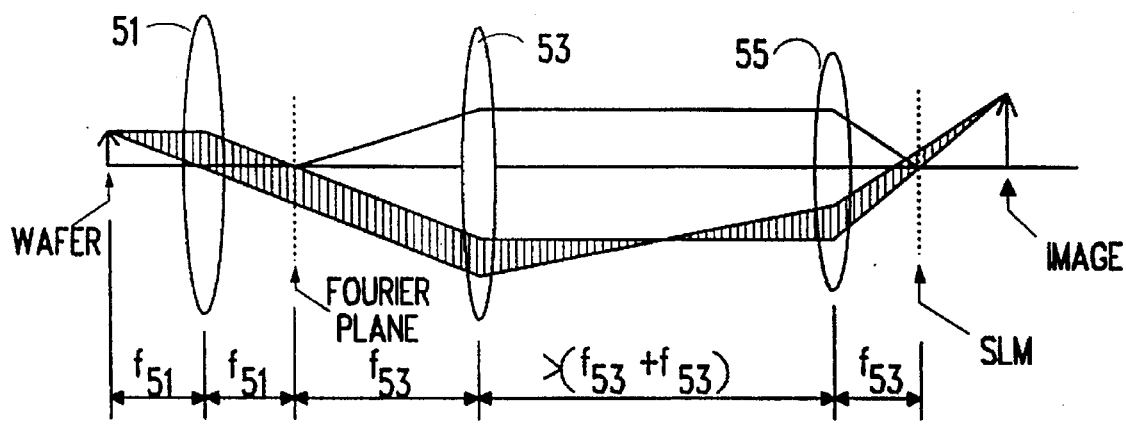
FIG. 3 is a ray trace of light from the patterned semiconductor wafer to the detector in FIG. 1.

A ray trace of the light path from wafer 13 to detector 25 is shown in FIG. 3. Also shown in FIG. 3 is the spacing of some of the components.

Figure 4:
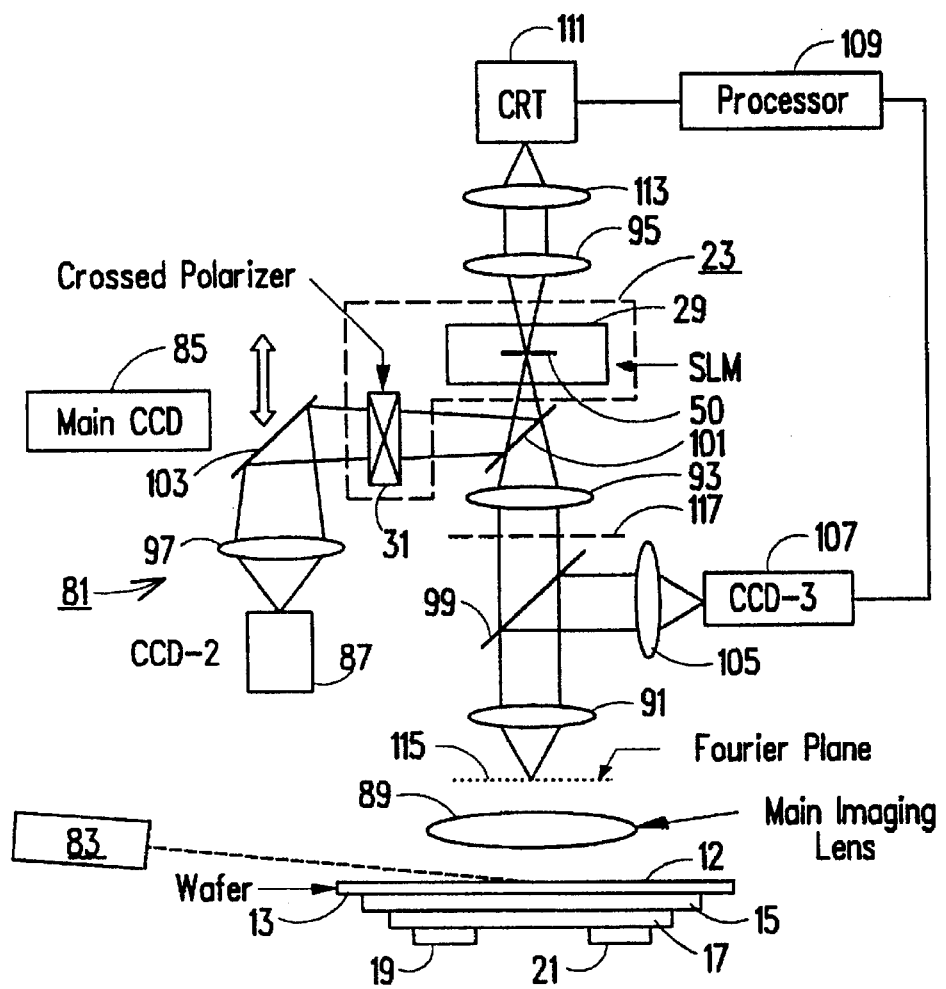
FIG. 4 is a schematic representation of another embodiment of the invention.

Referring now to FIG. 4 there is shown another embodiment of an apparatus constructed according to this invention, the apparatus being identified by reference numeral 81.

Apparatus 81 differs from apparatus 11 in that a portion of the Fourier diffraction pattern formed in the Fourier plane is not used directly as the write beam, as in apparatus 11, but, rather, is converted into electrical signals which are processed and then converted back to a video image which is then used as the write beam.

Apparatus 81 includes a light source 83, a first light detector 85, a second light detector 87, a first lens 89, a second lens 91, a third lens 93, a fourth lens 95, a fifth lens 97, a first beamsplitter 99, a second beamsplitter 101 and a third beamsplitter 103 corresponding, respectively to light source 21, light detector 25, light detector 27, first lens 51, second lens 53, third lens 55, fourth lens 57, fifth lens 59 beamsplitters 65 and 71 and movable mirror 73, respectively, in apparatus 11.

Apparatus 81 also includes a self-programmable Fourier mask 23.

However, instead of mirrors 67 and 69, apparatus 81 includes a sixth lens 105, a third light detector 107, a processor 109, a CRT 111 and a seventh lens 113. Detector 107 is identical in construction to detector 87.

Lens 105 in combination with lens 91 images the Fourier diffraction pattern formed in Fourier plane 115 of lens 89 into light detector 107 where the image is converted into a stream of digital electrical signals. The stream of digital electrical signals are processed in processor 109, as maybe desired. The processing may include raising the overall gain of the image or blocking out selected areas. The output of processor 109 is fed into CRT 111 which converts the digital electrical signals into a video image. The video image from CRT 111 is collected by lens 113 and then reimaged by lens 95 through glass 33 onto photoconductor 37 in spatial light modulator 29. At the same time, lens 91 in combination with lens 93 images the Fourier diffraction pattern through glass layer 45, transparent electrode 43 and liquid crystal 41 onto mirror 39. Lens 89 in combination with lens 91 forms an image of the area illuminated by light source 83 at image plane 117. The image formed at image plane 117 is then collected by lens 93 and passed through Fourier mask 85, using beamsplitter 101. The filtered image is then brought to focus at detector 85. The diffraction pattern at Fourier plane 115 is imaged at detector 87 after it passes through mask 23.

Figure 5:
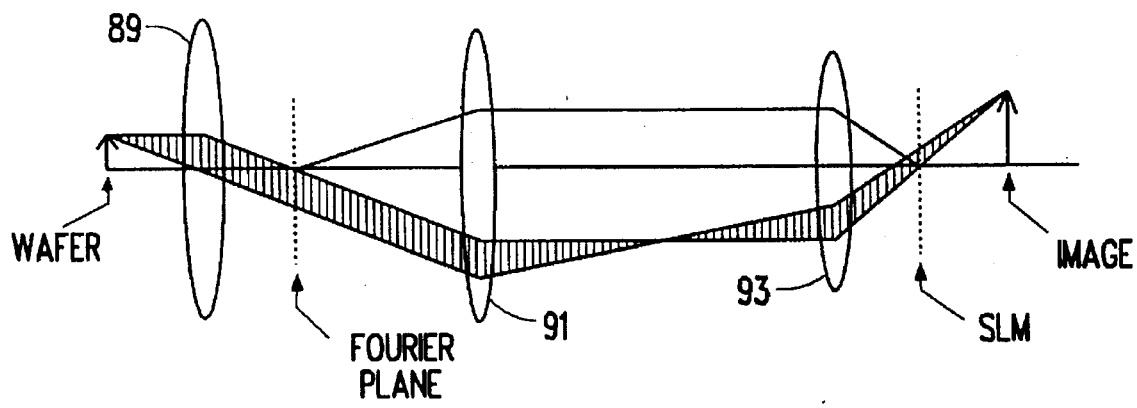
FIG. 5 is a ray trace of light from the patterned semiconductor wafer to the detector in the FIG. 4 embodiment of the invention.

A ray trace of light from wafer 13 to camera 91 is shown in FIG. 5.

The embodiments of the present invention recited herein are intended to be merely exemplary and those skilled in the art will be able to make numerous variations and modifications to it without departing from the spirit of the present invention. For example, an array of photodiodes can be used in place of any or each one of the cameras. Also, cameras 25 and 85 could be replaced by non-imaging detectors, such as a photomultiplier tube if an image of the area illuminated is not desired. All such variations and modifications are intended to be within the scope of the present invention as defined by the claims appended hereto.

What is claimed is:

1. Apparatus for detecting particles on a surface of a semiconductor wafer, said surface having repetitive patterns, the apparatus comprising:

a. means for illuminating an area on said surface with a beam of polarized light,
    b. a first lens for collecting light scattered from said area, said first lens forming a Fourier diffraction pattern of scattered light collected from said area, said light in said Fourier diffraction pattern being polarized,
    c. a Fourier mask for blocking light in said Fourier diffraction pattern where the intensity is above a predetermined threshold level and leaving in light in said Fourier diffraction pattern where the intensity is below said predetermined threshold level, said light in said Fourier diffraction pattern where the intensity is above said predetermined threshold level being indicative of background information and said light in said Fourier diffraction pattern where the intensity is below said predetermined threshold level being indicative of particle information, the Fourier mask including a spatial light modulator for rotating the polarization of light below said predetermined threshold level and a crossed polarizer for receiving light from the spatial light modulator and blocking light received whose polarization has not been rotated, said spatial light modulator being optically addressable and including a photoconductive layer which serves as an optical addressing material for a write beam and a liquid crystal layer which serves as a light modulating material for a read beam,
    d. means for imaging the Fourier diffraction pattern formed by the first lens onto the photoconductive layer in the spatial light modulator as the write beam and also onto the liquid crystal layer in the spatial light modulator as the read beam, the image on the photoconductive layer being aligned with the image on the liquid crystal layer,
    e. areas on the image on the photoconductive layer where the intensity of the image of the Fourier diffraction pattern is below said predetermined threshold level causing the polarization of corresponding areas of the image on the liquid crystal layer to be rotated 90 degrees, and
    f. a detector for detecting light collected by the first lens and not blocked by the Fourier mask.

2. The apparatus of claim 1, and further including a second lens and a third lens, said first lens and said second lens forming an image of the light scattered from the area in an intermediate image plane and said third lens forming an image at the detector of the image formed in the intermediate image plane.

3. The apparatus of claim 2, wherein said beam of light illuminating said area strikes said surface at grazing angle of incidence.

4. The apparatus of claim 3, and further including a second detector for detecting light corresponding to the Fourier diffraction pattern.

5. Apparatus for detecting particles on a surface of a semiconductor wafer, said surface having repetitive patterns, the apparatus comprising:

a. means for illuminating an area on said surface with a beam of polarized light,
    b. a first lens for collecting light scattered from said area, said first lens forming a Fourier diffraction pattern of scattered light collected from said area said light in said Fourier diffraction pattern being polarized,
    c. a Fourier mask for blocking light in said Fourier diffraction pattern where the intensity is above a predetermined threshold level and leaving in light in said Fourier diffraction pattern where the intensity is below said predetermined threshold level, said light in said Fourier diffraction pattern where the intensity is above said predetermined threshold level being indicative of background information and said light in said Fourier diffraction pattern where the intensity is below said predetermined threshold level being indicative of particle information, the Fourier mask means including a spatial light modulator for rotating the polarization of light below said predetermined threshold level and a crossed polarizer for receiving light from the spatial light modulator and blocking light received whose polarization has not been rotated, said spatial light modulator being optically addressable and including a photoconductive layer which serves as an optical addressing material and a liquid crystal layer which serves as a light modulating material, d. means for imaging the Fourier diffraction pattern formed by the first lens onto the photoconductive layer in the spatial light modulator, e. means for generating a video image of the Fourier diffraction pattern and then imaging the video image so generated onto the liquid crystal layer in the spatial light modulator, f. the image on the photoconductive layer being aligned with the image on the liquid crystal layer, and g. areas on the image of the photoconductive layer where the intensity of the image of the Fourier diffraction pattern is below said predetermined threshold level causing the polarization of corresponding areas of the image on the liquid crystal layer to be rotated 90 degrees, h. a detector for detecting light collected by said first lens and not blocked by said Fourier mask.

* * * * *